United States Patent [19]
McLain

[11] 3,982,425
[45] Sept. 28, 1976

[54] ULTRASONIC INSPECTION SYSTEM

[75] Inventor: Robert E. McLain, Woodland Hills, Calif.

[73] Assignee: Rockwell International Corporation, El Segundo, Calif.

[22] Filed: Jan. 14, 1974

[21] Appl. No.: 433,036

[52] U.S. Cl............................ 73/67.8 S; 73/71.5 US
[51] Int. Cl.²......................................... G01N 29/00
[58] Field of Search............ 73/67.8 S, 67.8 R, 67.9, 73/67.7, 67.6, 67.5 R, 71.5 US; 307/284, 246, 247 R

[56] References Cited
UNITED STATES PATENTS

| | | | |
|---|---|---|---|
| 2,842,959 | 7/1958 | Henry | 73/67.8 R X |
| 3,257,637 | 6/1966 | Henry | 73/67.7 |
| 3,282,086 | 11/1966 | McCorkindale et al. | 73/67.8 R |
| 3,324,313 | 6/1967 | Soroka | 307/284 |
| 3,387,257 | 6/1968 | Brech | 73/67.8 R X |
| 3,417,266 | 12/1968 | Webb | 307/263 |
| 3,518,455 | 6/1970 | Pearce et al. | 307/265 |
| 3,620,070 | 11/1971 | Collins | 73/67.8 R |
| 3,657,564 | 4/1972 | Hollis | 307/246 |
| 3,811,320 | 5/1974 | Cowell | 73/67.8 S |
| 3,828,609 | 8/1974 | Furon et al. | 73/67.8 S |

Primary Examiner—Richard C. Queisser
Assistant Examiner—Stephen A. Kreitman
Attorney, Agent, or Firm—L. Lee Humphries; Henry Kolin; Clark E. DeLarvin

[57] ABSTRACT

An ultrasonic inspection system is disclosed having a skate remotely controlled from a main console for positioning an ultrasonic transducer. A transmission line is used to couple drive pulses from the main control console to the transducer. Each drive pulse is generated at the console by timing means for firing a first silicon-controlled rectifier (SCR) to discharge a precharged capacitor into the line, and for firing a second SCR to shunt discharge current from the capacitor to ground. The line is terminated at its input end by its characteristic impedance. The length of the line may be changed without requiring any change at the transducer or the pulse generating circuit, except that the size of the precharged capacitor may be varied to assure delivery of a pulse of desired amplitude to the transducer.

13 Claims, 3 Drawing Figures

ULTRASONIC INSPECTION SYSTEM

BACKGROUND OF THE INVENTION

1. Field of the Invention

This invention relates to automated ultrasonic inspection systems, and is particularly directed to apparatus for pulsing a piezoelectric transducer from a remote station while performing in-service inspection of nuclear reactor coolant systems and the like.

2. Description of the Prior Art

Automated ultrasonic in-service inspection systems have been developed in the recent past for fast breeder reactors and both pressurized and boiling water reactors. The technical approach which has been followed features remotely controlled traveling instrument carriers, and computerized collection and storage of inspection data in a manner providing real time comparison against predetermined standards. The radiation levels experienced in components other than the reactor during in-service examination require that automated inspection systems be operated from a main control console which operates an instrument carrier from a remote position as far as 300 feet.

The philosophy adopted for the computer controlled instrument carrier has been to maintain as much as possible of the computer control electronics at the remote console. In practice, the instrument carrier (commonly referred to as a "skate") is provided with only enough structure to permit positioning the skate along a track adapted to fit the specific contour of the steam generator, reactor vessel, and the like, to be inspected. The details of the skate and track, and a method of mounting the track are disclosed in a copending U.S. application Ser. No. 248,466, filed Apr. 28, 1972, by Laurence S. Beller for an INSPECTION ANALYSIS SYSTEM, now U.S. Pat. No. 3,857,052 assigned to the assignee of this application.

In order to minimize the size and weight of the skate, only the piezoelectric transducer of the ultrasonic inspection system is mounted on the skate. The piezoelectric transducer is connected to the main control console through a flexible transmission line. The transducer is then periodically pulsed under control of the computer through the transmission line, and echoes sensed by the transducer following each pulse are carried back to the main computer console through the same transmission line.

In the past the automated ultrasonic inspection systems have used two separate, but similar techniques to pulse the ultrasonic transducer through the transmission line. In one technique, the piezoelectric transducer capacitance is placed in parallel with an input coil to form an LC tank circuit tuned to the resonant frequency of the transducer. This tuned circuit is triggered into resonance through the transmission line with a high-voltage pulse generator. For example, in one transducer pulsing arrangement, a capacitor of up to 2,400 picofarads of capacitance is charged to 1,000 volts at the remote console and discharged through a thyratron into the transmission line. In another arrangement three 330 picofarad capacitors are charged to 400 volts in parallel and discharged into the transmission line in series.

The problem with these prior art techniques is that a tuned circuit is relied upon to apply a voltage pulse to the transducer of consistently high amplitude for a consistent period each time the transducer is to transmit an ultrasonic wave. If the amplitude and duration of the applied pulse is not consistent, the transmitted ultrasonic wave will not be consistent, the consequence of which is that echoes received by the transducer will also not be consistent for a homogeneous body being inspected. It is, of course, evident that any inconsistencies in the received echoes will be interpreted as a variation in the body (vessel wall or other structural member) being inspected. Such variation would render the inspection data unreliable.

Serious problems are present in these techniques for pulsing a tuned circuit through a transmission line because precise tuning of the resonance must take into consideration the capacitance of the transmission line, and therefore its length. When a very long coaxial cable is used, a very large capacitance in the cable is connected to the tuned tank circuit. For example, 300 feet of RG59/U add 6900 picofarads of capacitance to the tuned circuit. The coil of the tuned circuit must be slug-tuned to the resonance frequency of the transducer, typically 2.25 MHz. This type of tuning for the tank circuit can only adjust for approximately 1,500 picofarads of capacitance. The tank circuit may also be adjusted by a variable capacitor within the adjustment range of 7.5 – 100 picofarads. In either case, the input cable is treated solely as a capacitance, and adding or subtracting short lengths of cable is taken care of by the tuning adjustment. However, when the length of the input cable is increased beyond a certain point (about 100 feet), it is no longer to be considered as a pure capacitance, but as a 75 ohm transmission line with a transit time of 1.5 nanoseconds per foot. Consequently, for a 300 foot cable, the transit time for a pulse is 450 nanoseconds, and any mismatches at either end of the line can cause reflections. Any reflection from the drive end back to the transducer would interfere with echo signals being received through the transmitter.

In these prior art techniques, the pulse generator is transferring the energy stored in a capacitor at the remote station of the main control console to the cable and the tuned circuit at the skate carrying the piezoelectric transducer. The efficiency of this energy transfer depends on the impedance transform of the circuit. Changing circuit values to increase the excitation voltage applied to the piezoelectric transducer can adversely affect other properties of the tuned circuit, such as repetition rate and pulse shape.

To avoid these problems of the prior art, it would appear to be necessary to place the pulse generator on the skate carrying the transducer for cable lengths in excess of about 100 feet. However, this solution is not feasible since the added pulse generator would increase the size and weight of the load on the skate so that it would then be necessary to provide a larger skate and heavier drive system for the skate. Another disadvantage is that an operator would not be able to make adjustments on the pulse generator to accommodate a longer output cable for the transducer, and an impedance match would still have to be made.

OBJECTS AND SUMMARY OF THE INVENTION

An object of this invention is to provide an automated ultrasonic inspection system with a piezoelectric transducer at a location remote from a main console at which an energizing pulse for the transducer is generated and accurately timed for transmission to the transducer over a transmission line, such as a coaxial cable, of any length between the main console and the transducer. Still another object of the invention is to provide an adjustable pulse generator and transmission line for a piezoelectric transducer in an arrangement which allows maximum energy of excitation into the transducer with any reasonable length of transmission line up to several hundred feet. Yet another object is to be able to adjust the pulse width and amplitude without any adjustments at the piezoelectric transducer at the remote end of a transmission line.

These and other objects of the invention are achieved by coupling an ultrasonic transducer to a pulse generator by a transmission line and terminating the transmission line by its characteristic impedance with a resistor at the input end of the transmission line. A capacitance at the end of the transmission line remote from the transducer is charged to a supply voltage, preferably through an emitter-follower to reduce charging time. To transmit a pulse to the transducer, the capacitor is coupled to the transmission line through a silicon-controlled rectifier triggered at the time the drive pulse for the transducer is to begin. A second silicon-controlled rectifier connected in parallel with the capacitor is turned on when the drive pulse is to terminate, thus quickly discharging the capacitor and terminating the drive pulse. The capacitor and distributed capacitance of the transmission line form a voltage divider at the end of the transmission line remote from the transducer. Consequently, the larger the capacitor, the greater the voltage impressed upon the transmission line so that precise control of the pulse amplitude is determined by the size of the capacitor and the capacitance of the transmission line. In view of that, the length of the transmission line may be changed without requiring any adjustment other than in the size of the capacitor to assure a pulse of desired amplitude that is accurately timed through operation of the silicon-controlled rectifiers. Following a drive pulse to the transducer, reflected signals picked up by the transducer are transmitted through the same transmission line and detected across the terminating resistor. The inspection receiver is coupled to the terminating resistor by a series resistor and diode limiter arrangement.

Pulse generator circuits per se are, of course, well known. See, for example, U.S. Pat. Nos. 3,324,313; 3,417,266; 3,518,455 and 3,657,564. However, the novel features that are considered characteristic of this invention are set forth with particularity in the appended claims. The invention will best be understood from the following description when read in connection with the accompanying drawings.

DESCRIPTION OF THE PREFERRED EMBODIMENTS

Figure 1:
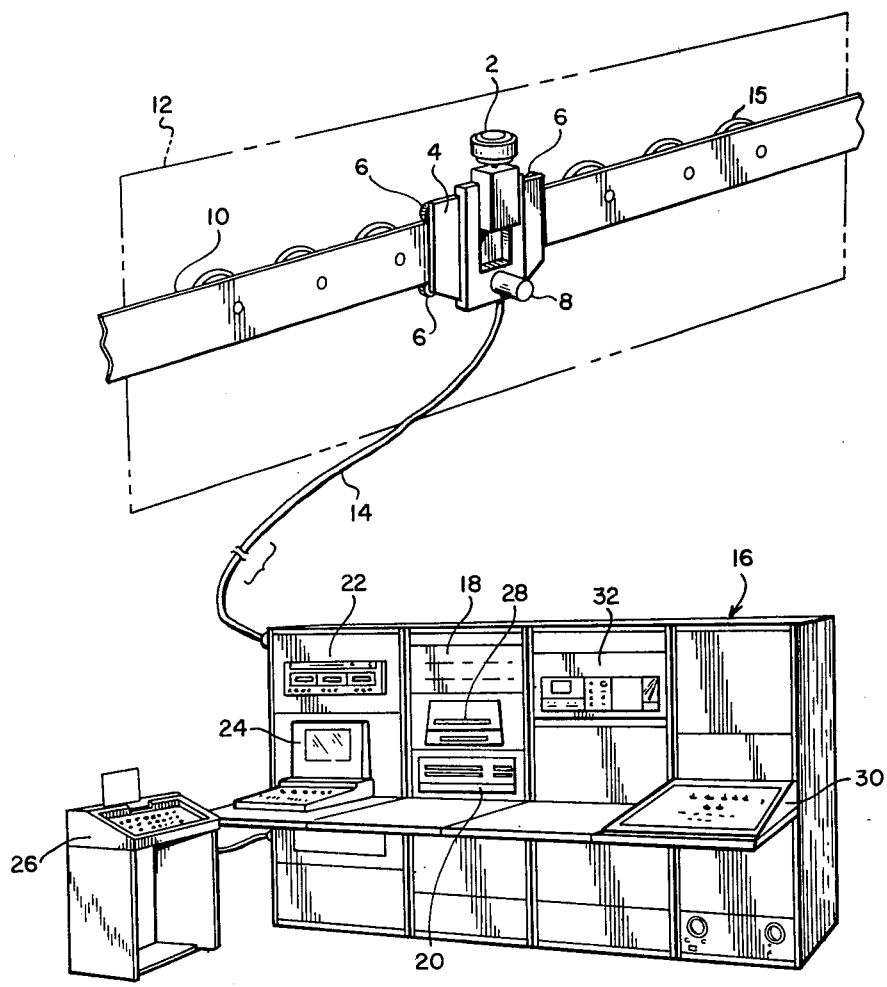
FIG. 1 is an isometric view of an inspection system embodying the present invention.

Referring to the drawings, FIG. 1 shows an automated ultrasonic inspection system comprising a piezoelectric transducer 2 carried by a skate 4 having wheels 6 driven by a motor 8 to cause the skate to carry the transducer along a track 10 to inspect a wall 12 of a reactor vessel, or the like, or some other structural member, such as the steel structure of a bridge, where periodic in-service inspection is required and it is not feasible to carry more of the inspection system electronics that the transducer on the skate. In such a case it is necessary to connect the transducer to the rest of the automated ultrasonic inspection system by a transmission line, such as a coaxial cable, included in a bundle of lines 14.

The details of the skate 4 and track 10, and the method of mounting the track on the item to be inspected, are disclosed in the aforementioned copending application. The track is constructed, or otherwise adapted, to fit the specific contour of the wall to be inspected, and then permanently attached to the wall or fastened to it with suitable magnets 15. By properly selecting and placing the track, just about any configuration can be inspected under control of a remotely located inspection console 16. As the skate 4 moves the transducer 2 along an inspection path in response to computer controlled signals over a separate line in the bundle 14 connected to the motor 8, ultrasonic inspection information is received at the inspection console through the transmission line. To inspect a rectangular area, additional skates may be used at each end of the track 10 to move each end along parallel tracks (not shown). In that case, magnets are employed only on the additional parallel tracks at each end of the track 10 so that the track 10 is free to move in a vertical direction as shown in FIG. 1, while the transducer is free to move on the track 10 along a horizontal direction.

The main inspection console at the remote site is designed specifically for in-service inspection. Through the use of a sufficiently long transmission line, the skate may be used to carry the transducer to remote areas where either manual access in impossible or too restricted for reliable inspection operations, or as suggested hereinbefore, to inspect a structural member at a location where it would not be feasible to carry any part of the main inspection console, such as for inspecting structural members of a steel bridge.

The skate concept has been employed extensively, not only for ultrasonic inspection, but also for automatic welding, machining and X-ray inspection of large components. However, what is of interest here is only the use of the skate concept for ultrasonic inspection. The problem which this invention solves is the delivery of a voltage pulse to the piezoelectric transducer 2 over the transmission line used to receive echoes of the ultrasonic pulses from range gated volume elements of the wall. Before describing the unique solution to the problem and all of the advantages of that solution, the overall system will first be described further with reference to FIG. 1.

The main control console indicated generally at 16 includes an analog-to-digital converter 18, a digital computer 20, a memory unit 22, a visual display unit 24, a teletype 26, a "hard copy" device 28, such as a tape printer, a manual control panel 30, and an inspection unit 32 for controlling the pulsing of the transducer 2 and visually displaying the echo signals received from the transducer 2. Typically, the inspection unit 32 may be a Reflectoscope, Model UM771, manufactured by the Sperry Division of Automation Industries.

In use, the transducer 2 mounted on the skate 4 is positioned by commands from the computer 20 to cause the transducer to scan along a predetermined path determined by the track 10. The echo signals received by the transducer 2 are transmitted to the inspection unit 32 over the transmission line and from there to the analog-to-digital converter 18. The converter consists of a circuit to range-gate samples of the echo signal for successive volume elements of the wall 12, means for integrating each sample, and means for converting the amplitude of the output from the integrator to digital form. The converter thus provides the interface between the ultrasonic transducer and the computer.

A circuit which generates a range-gate pulse is triggered by a synchronizing pulse derived from the inspection unit 32. This starts a time delay circuit. The length of the delay is determined by a digital command from the computer 20 and can be adjusted from approximately 0.1 to 300 microseconds after the transducer has been excited by a pulse from a pulse generator over the transmission line. At the end of this delay period, the video signal from the inspection unit 32 is gated into an integrator for a fixed length of time after which the amplitude of the integrated signal is held constant while it is converted to digital form.

The length of the gate is chosen by a front panel or computer control to correspond to a sound-path length, or range increment of about 0.5 inches. The length of the delay is chosen from speed-of-sound considerations in the wall 12 to correspond to the effective distance from the transducer to the particular volume element of the wall being inspected. The signal presented to the analog-to-digital converter corresponds to the average echo signal returning from a volume element of predetermined length and area, the area being a cross-sectional area determined by the diameter of the ultrasonic pulse beam, each volume element being located at a distance from the transducer determined by the delay setting.

The operating cycle is as follows. The computer 20 determines an initial delay setting corresponding to the first such volume element to be inspected, and sets the range gate to this value. The transducer is then pulsed a number of times, and each time the range gate provides the sample of the volume element to be inspected. When a sufficient number of samples from this volume element have been obtained, the next increment in delay is commanded and a new set of samples is obtained. The process is continued until the most distant volume element at the current transducer position has been inspected. The transducer is then moved to a new position and the cycle is repeated.

Since the range gate is timed from the excitation time of the transducer, that is from the time of the drive pulse applied to the transducer, it is important that the timing of the drive pulse, and its pulse width, be accurately maintained from pulse to pulse for inspection of a given volume element and for each succeeding volume element. Otherwise, the echo return cannot be accurately defined as coming from a particular volume element. The echo return will, for homogeneous material of the wall being inspected, be of a constant amplitude. Any variation from the constant amplitude indicates some change in the material as inspection progresses from element to element, and from one position of the transducer to the next, so that any change may indicate a defect, depending upon whether or not a change should be present as indicated by comparison with pre-service inspection data. For example, in a nuclear reactor vessel, all welds are inspected prior to installation of the vessel, and the complete ultrasonic inspection data is stored for comparison with in-service inspection data.

During an in-service inspection, the computer locates the stored pre-service data and the signal from each volume element is tested statistically against the pre-service data. If there are no significant ultrasonic indications of a change, the data are printed out. If there is a significant change from pre-service data, the computer alerts the operator and directs the skate to search for the outlines of the affected area in fine steps. The indications of change are thus mapped out and compared to pre-service data. Locations, dimensions and magnitude are printed out, and a properly scaled plan or section map is displayed on an oscilloscope from which a film record can be obtained. Additional inspection procedures might also be used, such as obtaining ultrasonic test data from a calibration block and comparing all measurements of the wall under inspection against such a calibration block both in pre-service and in-service inspection to determine whether there is any significant change from such a calibration block.

Since the ultrasonic inspection system is based upon any change in amplitude of the received echo, any change in the amplitude of the pulse transmitted by the transducer will affect the sensitivity and overall accuracy of the inspection system. Consequently, it is important that the drive pulse to the transducer be accurately controlled in time and amplitude.

As noted hereinbefore, techniques for controlling both time and amplitude of the drive pulse for the ultrasonic transducer have heretofore been restricted to transmission lines of relatively short lengths, on the order of 100 feet, and it is very often desirable to place the main console at greater distances from the ultrasonic transducer, such as at a distance of 300 feet or more. The manner in which the present invention provides accurate control of both the timing and amplitude of drive pulses over a transmission line of a given length is limited only by the overall consistent attenuation of each pulse in a unit length of the transmission line. However, that is not a serious limitation because, within reason, a longer transmission line can be accommodated by simply increasing the amplitude of the drive pulse without departing from the teachings of the present invention.

Figure 2:
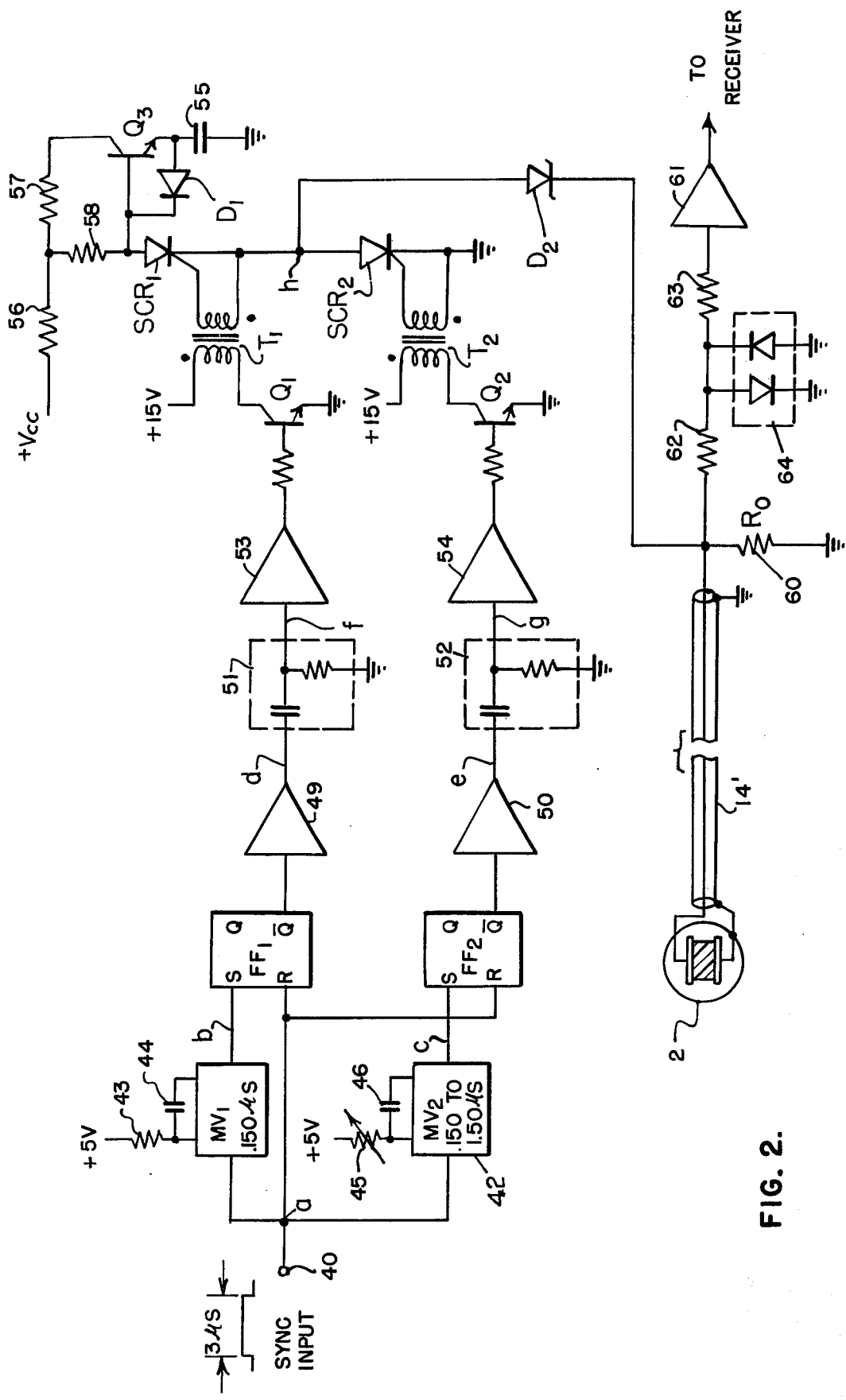
FIG. 2 is a schematic diagram of the present invention.

Referring now to FIG. 2, a pulse generator is disclosed for driving the piezoelectric transducer 2 through a transmission line of any length shown as a coaxial cable 14'. The timing of a drive pulse is established by the leading edge of a sync input pulse at a terminal 40. The sync input pulse is preferably a 3 microsecond pulse generated at a desired rate of up to about 4 kilohertz with a sharp leading edge to trigger a pair of multivibrators $MV_1$ and $MV_2$. The pulse width of the drive pulse delivered to the transducer 2 over the transmission line is accurately established by the RC timing circuits of the multivibrators. The RC timing period of the multivibrator $MV_1$ is fixed at 150 nanoseconds by a resistor 43 and capacitor 44. The RC timing period of the multivibrator $MV_2$ is set by a variable resistor 45 and capacitor 46 between 150 nanoseconds and 1.5 microseconds.

The leading edge of the sync pulse applied at the terminal 40 also resets a pair of flip-flops $FF_1$ and $FF_2$. The trailing edge of the output pulses from the multivibrators $MV_1$ and $MV_2$ sets the flip-flops $FF_1$ and $FF_2$ in that order, the flip-flop $FF_1$ being set at a fixed period of 150 nanoseconds following the leading edge of the sync input pulse, and the flip-flop $FF_2$ being set at an adjustable time from 150 nanoseconds to 1.5 microseconds following the leading edge of the sync input pulse.

Figure 3:
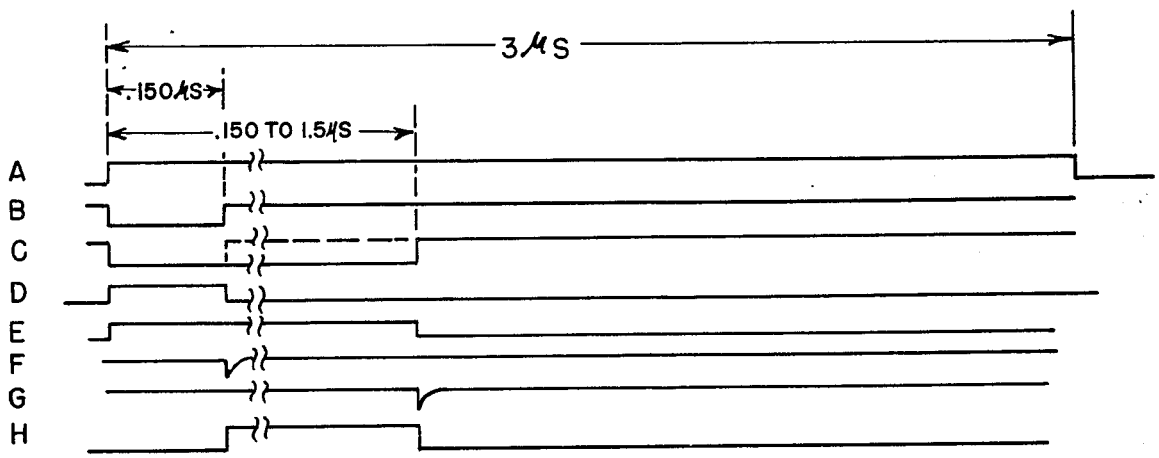
FIG. 3 is a waveform diagram useful in understanding the operation of the present invention.

Since the flip-flops are set at different times by the multivibrators $MV_1$ and $MV_2$, the time at which the flip-flop $FF_1$ is set may be used to initiate the drive pulse to the transducer 2, and the time at which the flip-flop $FF_2$ is set may be used to terminate the drive pulse as may be seen in FIG. 3, a timing diagram showing waveforms A through H at respective points a through h in FIG. 2. In each case, regardless of the RC timing period set for the multivibrator $MV_2$, the drive pulse starts 150 nanoseconds after the sync pulse is applied to the terminal 40.

It would be possible to use the sync pulse at the terminal 40 to directly set the flip-flop $FF_1$, and thereby initiate the drive pulse simultaneously with the sync pulse. The RC timing period of the multivibrator $MV_2$ could then be set to provide the desired pulse width. However, the flip-flop $FF_1$ is set through the multivibrator $MV_1$ so that the signal path employed for initiating the pulse will be identical to the signal path used for terminating the pulse, except for a difference in the RC timing circuits of the multivibrators, in order that any change in the period established by the multivibrator $MV_2$ caused by changes in the temperature of the environment will also affect the timing of the start of a drive pulse. For example, if an increase in temperature decreases the RC timing period of the multivibrator $MV_2$, a substantially equal decrease will occur in the RC timing period of the multivibrator $MV_1$. The net result will be that a pulse transmitted to the transducer over the transmission line 14' will start earlier, but will be of substantially the same width as before any change in temperature. If the leading edge of the drive pulse transmitted to the transducer 2 is then detected and used to time the range gate, any change in the RC timing period of the multivibrators will have no effect on the timing of the range gates which define the volume elements inspected. However, it would be possible to initiate timing of the range gates through another circuit comprised of a multivibrator triggered by the leading edge of the sync pulse and a flip-flop set, or reset, by the output of the multivibrator. Any change in the RC timing of the multivibrators $MV_1$ and $MV_2$ would affect the RC timing of this third multivibrator and would serve to maintain synchronization between the range gates and the drive pulses without the need to detect the leading edge of the drive pulses.

The complementary ($\bar{Q}$) outputs of the flip-flops $FF_1$ and $FF_2$ are amplified and inverted from negative-going square waves to positive-going square waves by amplifiers 49 and 50. The negative-going steps in the trailing edges of those square waves shown in waveforms D and E of FIG. 3, are differentiated by differentiating circuits 51 and 52 to provide sharp negative pulses to the input terminals of inverting amplifiers 53 and 54. The positive output pulses of those amplifiers are applied to the base electrodes of NPN transistors $Q_1$ and $Q_2$. The transistors invert the pulses to provide negative-going pulses across the primary windings of pulse transformers $T_1$ and $T_2$, but the transformers are wound to reinvert the polarity of the pulses, thereby providing positive gate pulses across secondary windings of the transformers to fire silicon-controlled rectifiers $SCR_1$ and $SCR_2$ at the respective times of pulses shown in waveforms F and G of FIG. 3 at points $f$ and $g$ of FIG. 2. The result is a drive pulse at point h as shown in waveform H of FIG. 3.

The manner in which the drive pulse is actually generated will now be described in more detail. Since the multivibrator $MV_1$ will always be set first (150 nanoseconds following the leading edge of the sync pulse at the input terminal 40), a pulse will be coupled by the transformer $T_1$ to fire the $SCR_1$ and cause a charged capacitor 55 to discharge through a $p$-$n$ junction diode $D_1$, the $SCR_1$ and a zener diode $D_2$. These diodes, $D_1$ and $D_2$, and the $SCR_1$ are all properly poled, as shown, for discharging the capacitor 55 into the transmission line. At a later time set by the adjustable RC timing period of the multivibrator $MV_2$, the flip-flop $FF_2$ is set to trigger the $SCR_2$ through the transformer $T_2$. The $SCR_2$ is connected to circuit ground so that once it fires, current to the transmission line from the capacitor 55 through the $SCR_1$ is shunted to circuit ground, thereby quickly terminating the drive pulse to the transducer. When the capacitor 55 has discharged sufficiently, the voltage across the SCRs will not provide sustaining current sufficient to maintain them conducting. Once they stop conducting, an NPN transistor $Q_3$ connected as an emitter-follower, will start to conduct to recharge the capacitor 55 toward a positive voltage $+V_{cc}$ through resistors 56 and 57. A resistor 58 connected to a junction between the resistors 56 and 57 biases the base of the transistor $Q_3$ positive with respect to its emitter to cause it to conduct until the capacitor is charged to a level equal to the supply voltage $+V_{cc}$, less the IR drop in the charging current path. It should be noted that the $p$-$n$ junction between the base and the emitter of the transistor $Q_3$ is poled opposite the $p$-$n$ junction of the diode $D_1$.

The transmission line 14' is terminated at the drive end thereof with its characteristic impedance $R_0$ by a resistor 60 connected to circuit ground. For a 75 ohm coaxial cable, such as an RG59/U cable, the terminating resistor 60 will be a 75 ohm resistor. The opposite end of the transmission line could also be terminated by the characteristic impedance of the transmission line. In that case, reflections would be prevented at both ends of the transmission line. For most efficient transfer of energy to the transducer, a close match between the line and the transducer is desired.

In the embodiment illustrated, only the input end of the transmission line is terminated with its characteristic impedance because a single reflection of the drive pulse back from the transducer 2 will not interfere with the transducer as an echo pick-up device. This is so because any echo returns will necessarily be received by the transducer 2 after the reflected pulse begins traveling back through the transmission line. Consequently, the single reflection back from the transducer to the input of the transmission line will be dissipated across the resistor 60 by the time the echo signals are received at the input end of the transmission line (point $h$). The zener diode $D_2$ which couples the $SCR_1$ to the transmission line 14' will prevent any reflected pulse from damaging either of the SCRs.

Received echo signals from the transducer 2 are coupled to a reciever preamplifier 61 through resistors 62 and 63. A diode limiter 64 is connected between the junction of the resistors 62 and 63 and circuit ground. The function of that limiter is to limit the amplitude of any pulse of either polarity to the amplifier 61. That is for the purpose of protecting the amplifier 61 from any damage due to the amplitude of the drive pulse. The output of the amplifier 61 is connected to an ultrasonic inspection system receiver.

From the foregoing it is evident that the amplitude of each drive pulse is accurately maintained by the charge across the capacitor 55, and that the width of each pulse is accurately maintained by the multivibrators $MV_1$ and $MV_2$. As noted hereinbefore, any variation in the RC timing period of one multivibrator will also occur in the other so that the width of each drive pulse is not affected by changes in ambient temeprature, nor in the aging of circuit components. The same is true of the signal path to the gate of the $SCR_1$ vis-a-vis the signal path to the gate of the $SCR_2$.

The advantages of this invention are: the ability to drive long transmission lines, and to change the length of the transmission line without having to make any change at the transducer; more stable drive pulses, both in amplitude and width; higher amplitude drive pulses more easily achieved by simply selecting a larger capacitor to place in parallel with the transmission line by the operation of the SCRs; and a higher signal-to-noise ratio due to the greater stability of drive pulse in both width and amplitude. The most important advantages are an adjustable pulse for excitation of the ultrasonic transducer with an independent changeable transmission line length. The slope of the pulse generated can be easily adjusted to accommodate common 1 MHz and 5 MHz ultrasonic transducers, or any other piezoelectric transducer. This is also an important advantage because of the many different piezoelectric transducers now available using ferroelectric ceramics such as barium titanate or lead titanate zirconate, as an alternative to piezoelectric crystals.

Although a particular embodiment of the invention has been described and illustrated herein, it is recognized that modifications and variations may readily occur to those skilled in the art. For example, although the multivibrators, flip-flops and amplifiers are illustrated as discrete functional elements, they could be provided as integrated circuits on a single semiconductor chip, and in the preferred embodiment they would be using the designs of available circuits which yield the optimum in speed for switching the states of the outputs of the functional circuits. A common substrate for all integrated circuits would provide optimum tracking of the two channels in respect to variations in response due to changes in ambient temperature. A good compromise would be a common substrate for the multivibrators and a common substrate for the flip-flops, or at least for the flip-flops. Dual flip-flop packages are readily available from manufacturers of integrated circuits. Operation of each multivibrator is largely determined by its RC timing circuit which is generally made of discrete elements, even if integrated circuits are used, in order to be able to select the RC time constant by changing or varying the discrete resistor and capacitor. However, by mounting both integrated circuit packages on a common heat sink, and otherwise taking care that both channels are subjected to the same ambient temperature, satisfactory performance can be expected. Consequently, it is intended that the invention be interpreted to include such and other modifications and variations, and that its scope be determined in accordance with the claims hereof.

What is claimed is:

1. In an ultrasonic inspection system having means for remotely controlling the position of an ultrasonic transducer from a console that is situated at least about 100 feet away, said positioning means carrying only an ultrasonic transducer connected to said console by a transmission line of arbitrary length through which said console energizes said transducer with high-voltage pulses, and through which said console receives from said transducer low-voltage echo pulses, means at said console for transmitting an energizing pulse to said transducer through said transmission line, said pulse generating means being comprised of a capacitor, means for precharging said capacitor prior to generating each pulse, first timed switching means for discharging said capacitor into said transmission line at the time a drive pulse is to begin, and second timed switching means for shunting discharge current from said capacitor away from said transmission line when a drive pulse is to terminate, whereby transmission lines normally used over short distances may be extended to over 100 feet without requiring any change at said transducer, and the system still remains operative.

2. Apparatus as defined in claim 1 wherein said first timed switching means for discharging said capacitor into said transmission line is comprised of a first silicon-controlled rectifier and means for firing said first silicon-controlled rectifier in response to a synchronizing pulse, and said second timed switching means for shunting discharge current away from said transmission line is comprised of a second silicon-controlled rectifier and delay means for firing said second silicon-controlled rectifier in response to said synchronizing pulse.

3. Apparatus as defined in claim 2 wherein said means for firing said first and second silicon-controlled rectifiers are separate, and each includes a separate but similar delay means for firing the separate silicon-controlled rectifiers, the delay means for each silicon-controlled rectifier being adapted to begin timing a delay on the same edge of said sync pulse but for a different delay period, whereby the duration of a drive pulse generated is determined by the difference in delay periods of said separate delay means, and any change in the delay period of one due to changing conditions will appear substantially the same in the delay period of the other.

4. Apparatus as defined in claim 2 wherein said means for precharging said capacitor comprises an emitter-follower transistor.

5. Apparatus as defined in claim 4 wherein said transistor has its base connected to its emitter by a diode poled opposite the base-emitter junction of said transistor, its emitter connected to said capacitor, its collecter connected to a source of collector voltage by two load resistors in series, a resistor connected between said base and a junction between said series load resistors, and its base is connected to a junction between said silicon-controlled rectifiers and said capacitor, whereby said capacitor recharges automatically when conduction through said silicon-controlled rectifiers becomes extinguished due to discharge of said capacitor below a predetermined level.

6. A system for performing in-service inspection of volume elements of a wall or other structural member comprising:

positioning means for mounting said transducer on said member and moving said transducer to successive positions along a predetermined inspection path on said member, a main console that is situated at least about 100 feet away from said member for controlling said positioning means, a flexible transmission line of arbitrary length connected between said transducer and said console for transmitting voltage drive pulses from said console to said transducer, and pulse generating means at said console for generating at said console said drive pulses, said pulse generating means including:

a capacitor, means for precharging said capacitor prior to generating each pulse, first timed switching means for discharging said capacitor into said transmission line at the time a drive pulse is to begin, and second timed switching means for shunting discharge current from said capacitor away from said transmission line when a drive pulse is to terminate, whereby transmission lines normally used over short distances may be extended to over 100 feet without requiring any change at said transducer and the system still remains operative.

7. Apparatus as defined in claim 6 wherein said first timed switching means for discharging said capacitor into said transmission line is comprised of a first silicon-controlled rectifier and means for firing said first silicon-controlled rectifier in response to a synchronizing pulse, and said second timed switching means for shunting discharge current away from said transmission line is comprised of a second silicon-controlled rectifier and delay means for firing said second silicon-controlled rectifier in response to said synchronizing pulse.

8. Apparatus as defined in claim 7 wherein said means for firing said first and second silicon-controlled rectifiers are separate, and each includes a separate but similar delay means for firing the separate silicon-controlled rectifiers, the delay means for each silicon-controlled rectifier being adapted to begin timing a delay on the same edge of said sync pulse but for a different delay period, whereby the duration of a drive pulse generated is determined by the difference in delay periods of said separate delay means, and any change in the delay period of one due to changing conditions will appear substantially the same in the delay period of the other.

9. Apparatus as defined in claim 7 wherein said means for precharging said capacitor comprises an emitter-follower transistor.

10. Apparatus as defined in claim 9 wherein said transistor has its base connected to its emitter by a diode poled opposite the base-emitter junction of said transistor, its emitter connected to said capacitor, its collector connected to a source of collector voltage by two load resistors in series, a resistor connected between said base and a junction between said series load resistors, and its base is connected to a junction between said silicon-controlled rectifiers and said capacitor, whereby said capacitor recharges automatically upon conduction through said silicon-controlled rectifiers being extinguished due to discharge of said capacitor below a predetermined level.

11. In an ultrasonic inspection system having means for remotely controlling the position of an ultrasonic transducer from a console situated at least about 100 feet away, said positioning means carrying only an ultrasonic transducer connected to said console by a transmission line of arbitrary length through which said console energizes said transducer with high-voltage pulses, and through which said console receives from said transducer low-voltage echo pulses, the combination comprising a skate remotely controlled from said main console for positioning an ultrasonic transducer, a pulse generating means located at said console for producing timed drive pulses required to cause said transducer to transmit a sonic wave, and connected to said transducer through said transmission line, said pulse generating means comprising timing means for firing a first silicon-controlled rectifier to discharge a precharged capacitor into said transmission line when a drive pulse is to be generated and for firing a second silicon-controlled rectifier to shunt discharge current from said capacitor to ground when said drive pulse being generated is to terminate, whereby transmission lines normally used over short distances may be extended to over 100 feet without requiring any change at said transducer, and the system still remains operative.

12. In an ultrasonic inspection system having means for remotely controlling the position of an ultrasonic transducer from a console at least about 100 feet away, said positioning means carrying only an ultrasonic transducer connected to said console by a transmission line of arbitrary length through which said console energizes said transducer with high-voltage pulses, and through which said console receives from said transducer low-voltage echo pulses, means for transmitting an energizing pulse to said transducer through said transmission line, comprising a capacitor, means for precharging said capacitor, first timed switching means for discharging said capacitor into said transmission line at the time a drive pulse is to begin, and second timed switching means for shunting discharge current from said capacitor away from said transmission line when a drive pulse is to terminate, whereby transmission lines normally used over short distances may be extended to over 100 feet without requiring any change at said transducer, and the system still remains operative, said timed switching means for discharging said capacitor into said transmission line being comprised of a first silicon-controlled rectifier and means for firing said first silicon-controlled rectifier, and said timed switching means for shunting discharge current from said capacitor away from said transmission line being comprised of a second silicon-controlled rectifier and means for firing said second silicon-controlled rectifier.

13. Apparatus as defined in claim 12 wherein said means for firing said first and second silicon-controlled rectifiers are separate, and each includes a separate but similar delay means for firing the separate silicon-controlled rectifiers in response to a single input timing pulse, the delay means for each silicon-controlled rectifier being adapted to begin timing a delay on the same edge of said input pulse but for a different delay period, whereby the duration of a drive pulse transmitted to said transducer over said line is determined by the difference in delay periods of said separate delay means, and any change in the delay period of one due to changing conditions common to both will appear substantially the same in the delay period of the other.

* * * * *